United States Patent
Barreca et al.

(10) Patent No.: US 10,689,332 B2
(45) Date of Patent: Jun. 23, 2020

(54) RACEMIC BETA-AMINOSULFONE COMPOUNDS

(71) Applicant: Quimica Sintetica, S.A., Barcelona (ES)

(72) Inventors: Giuseppe Barreca, Montevecchia (IT); Giovanni Marras, Galliate (IT); Fabio Morana, Novara (IT)

(73) Assignee: Quimica Sintetica, S.A., Barcelona (ES)

( * ) Notice: Subject to any disclaimer, the term of this patent is extended or adjusted under 35 U.S.C. 154(b) by 0 days.

(21) Appl. No.: 16/500,673

(22) PCT Filed: Mar. 28, 2018

(86) PCT No.: PCT/EP2018/057894
§ 371 (c)(1),
(2) Date: Oct. 3, 2019

(87) PCT Pub. No.: WO2018/184933
PCT Pub. Date: Oct. 11, 2018

(65) Prior Publication Data
US 2020/0087254 A1     Mar. 19, 2020

(30) Foreign Application Priority Data

Apr. 4, 2017   (EP) .................... 17382174

(51) Int. Cl.
| | | |
|---|---|---|
| C07C 315/00 | (2006.01) | |
| C07C 317/00 | (2006.01) | |
| C07C 261/00 | (2006.01) | |
| C07C 315/04 | (2006.01) | |
| C07C 251/16 | (2006.01) | |
| C07C 317/28 | (2006.01) | |

(52) U.S. Cl.
CPC .......... *C07C 315/04* (2013.01); *C07C 251/16* (2013.01); *C07C 317/28* (2013.01)

(58) Field of Classification Search
CPC .... C07C 315/04; C07C 318/28; C07C 251/16
See application file for complete search history.

(56) References Cited

FOREIGN PATENT DOCUMENTS

| WO | WO 2000/025777 A1 | 5/2000 |
|----|-------------------|--------|
| WO | WO 2013/126360 A2 | 8/2013 |
| WO | WO 2018/184933 A1 | 10/2018 |

OTHER PUBLICATIONS

Das et al., "A Mild and Efficient Catalytic Mannich-Type Reaction as a Simple Access to N-Benzyloxycarbonylbeta-Amino Ketones?," Synthesis, vol. 2010, No. 12, pp. 2057-2062 (2010).
Huang, et al. "Catalytic Asymmetric Synthesis of Tri-substituted Aziridines," Journal of the American Chemical Society, vol. 133, No. 23, pp. 8892-8895 (2011).
Huang, et al. "Catalytic Asymmetric Synthesis of Tri-substituted Aziridines: Supporting Information" Department of Chemistry, Michigan State University, pp. 1-58 (2011).
International Search Report and Written Opinion corresponding to International Application No. PCT/EP2018/057894 dated May 28, 2018.

*Primary Examiner* — Sikarl A Witherspoon
(74) *Attorney, Agent, or Firm* — Jenkins, Wilson, Taylor & Hunt, P.A.

(57) ABSTRACT

It is described an industrially viable and advantageous process for the preparation of racemic beta-aminosulfone (1), an useful intermediate for the preparation of N-(2-((1S)-1-(3-ethoxy-4-methoxyphenyl)-2-(methylsulfonyl)ethyl)-2,3-dihydro-1,3-dioxo-1H-isoindol-4-yl)acetamide, also known as Apremilast, the latter being suitable for use in methods of treating, preventing and/or managing psoriasis or psoriatic arthritis.

18 Claims, No Drawings

RACEMIC BETA-AMINOSULFONE COMPOUNDS

FIELD OF THE INVENTION

The present invention provides an industrially viable and advantageous process for the preparation of racemic beta-aminosulfone (1) depicted below, an useful intermediate for the preparation of N-(2-((1S)-1-(3-ethoxy-4-methoxyphenyl)-2-(methylsulfonyl)ethyl)-2,3-dihydro-1,3-dioxo-1H-isoindol-4-yl)acetamide, also known as Apremilast (compound having the formula shown below), the latter being suitable for use in methods of treating, preventing and/or managing psoriasis or psoriatic arthritis.

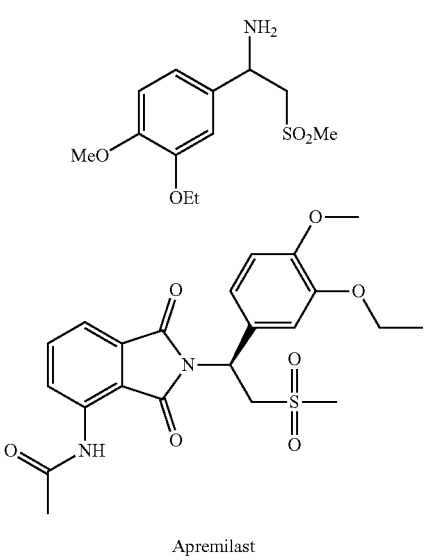

Apremilast

BACKGROUND OF THE INVENTION

The synthesis of sulfone compounds and in particular beta-aminosulfone compounds is of interest because these compounds may be particularly useful in the preparation of molecules with a potential for biological activities such as alfa-amino acids, uridines, adenosines, beta-lactams, etc.

The synthesis of sulfone compounds and in particular beta-aminosulfone compounds may thus provide useful intermediates for the synthesis of anti-inflammatory agents, preferably active for the treatment of psoriasis or psoriatic arthritis such as Apremilast.

Patent application WO 00/025777 A1 describes the synthesis of racemic beta-aminosulfone (1) and derivatives thereof, as illustrated in Scheme 1 below.

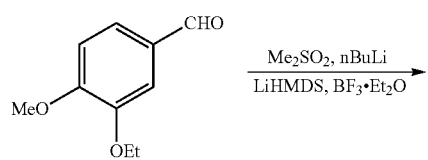

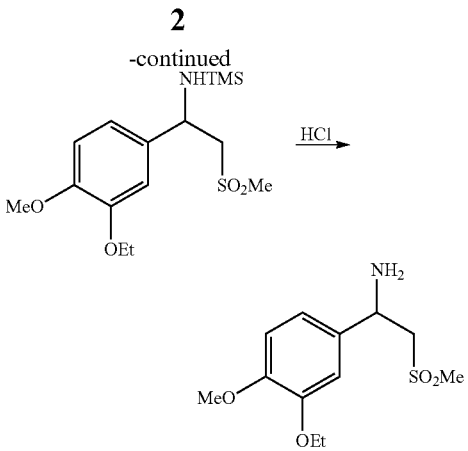

However, the overall synthetic route is characterized by several steps and low yield and selectivity, and uses expensive as well as hazardous materials, such as $BF_3 \cdot Et_2O$, very difficult to handle at the industrial scale.

Patent application WO 2010/030345 A2 describes the synthesis of racemic beta-aminosulfone (1) and derivatives thereof, as illustrated in the overall Scheme 2 below.

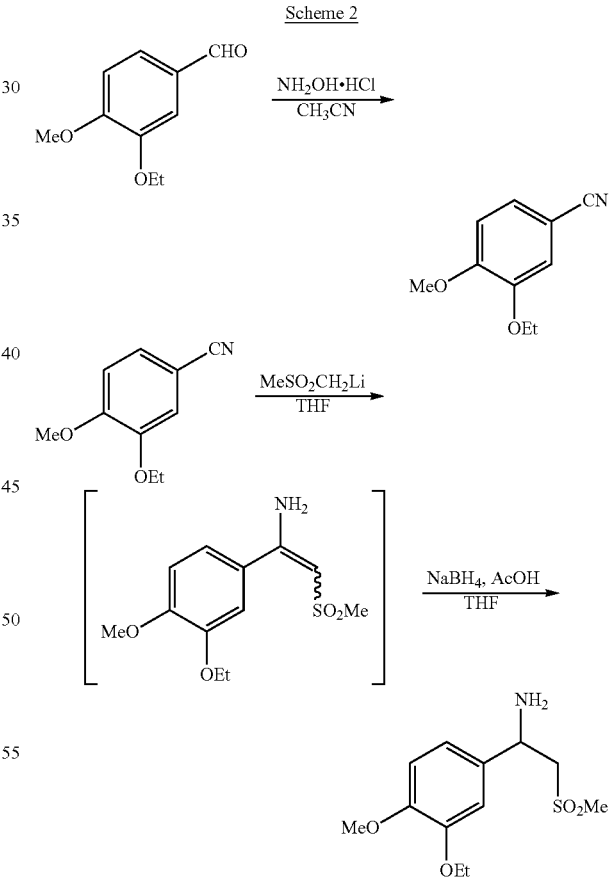

Although characterized by higher yields, this process too requires several steps to build the main molecular skeleton and using hydroxylamine could be a hazardous drawback anyway. Interestingly, the racemic form of beta-aminosulfone (1) can be prepared according to the overall route illustrated in Scheme 3 depicted below.

3

Scheme 3

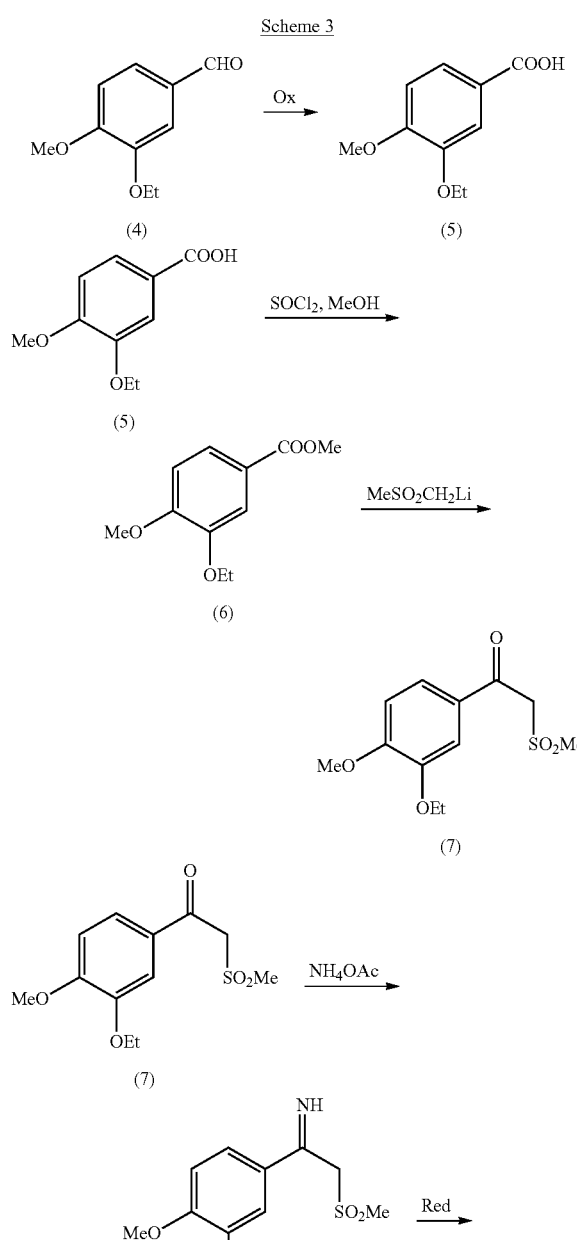

4 application CN 105348172 A describes the synthesis of racemic beta-aminosulfone (1), as illustrated in the overall Scheme 4 below.

Scheme 4

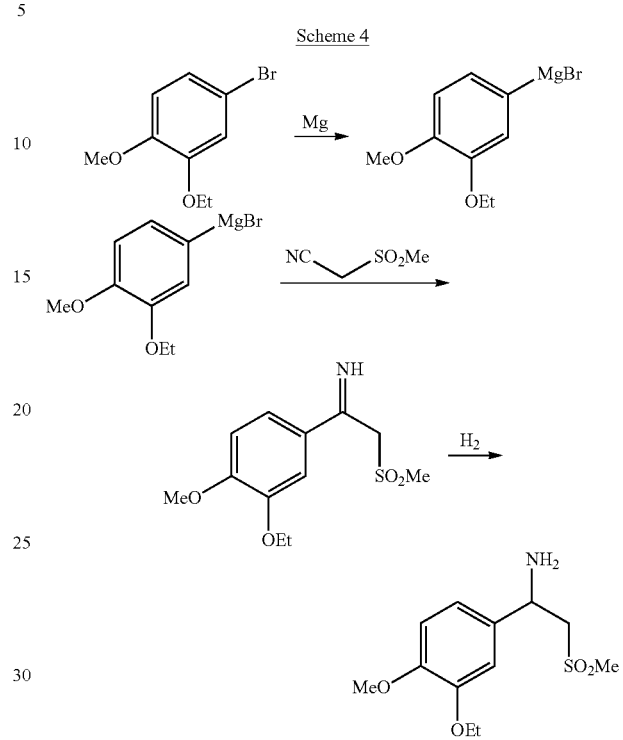

Although characterized by higher yields, once again these processes do not provide short and simple processes for preparing compound (1). Alternative methods for the preparation of racemic beta-aminosulfone (1), particularly for manufacturing large scale production, are thus desirable.

Object of the present invention is to provide a short, simple, cost-effective, environmentally friendly and industrially suitable synthetic process for preparing racemic beta-aminosulfone intermediate (1) which starts from simple and commercially available reagents.

SUMMARY OF THE INVENTION

This object is achieved with the present invention that, in a first aspect thereof, relates to a process for preparing a beta-aminosulfone (1)

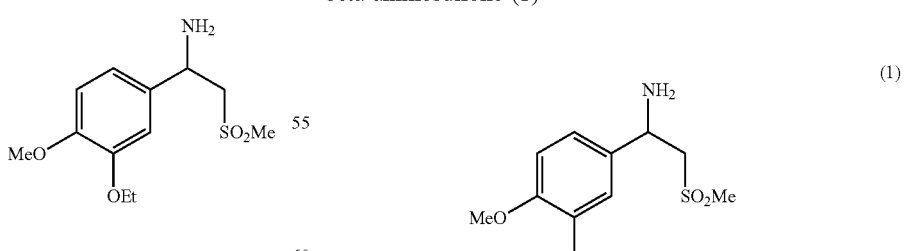

(1)

Oxidation of (4) to (5) can be carried out according to methods commonly known in the field of organic chemistry. The obtained carboxylic acid (5) is then converted into the corresponding methyl ester (6), in its turn transformed into keto-sulfone (7) following the teachings of patent application WO 2013/126360 A2. Finally, (7) is converted into the desired racemic beta-aminosulfone via reduction of imine (8) in accordance with commonly known methods. Patent said process comprising the steps of:

a) reacting 3-ethoxy-4-methoxybenzaldehyde (9) with a compound of formula $R^1$—$NH_2$ and a compound of formula $R^2$—S(O)OH or a salt thereof to obtain an aminosulfone of formula (2):

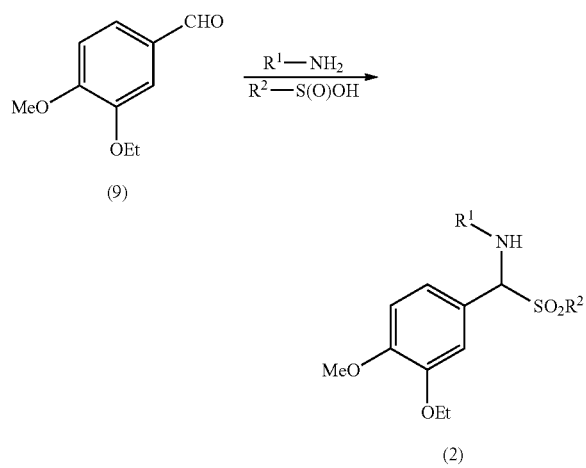

(9)

(2)

wherein:
R¹ is an amino protecting group; and
R² is a C1-C6 alkyl, a substituted C1-C6 alkyl, a C6-C10 aryl or a substituted C6-C10 aryl;
b) converting the aminosulfone of formula (2) into a sulfone of formula (3) by treatment with a carbanion derived from dimethyl sulfone:

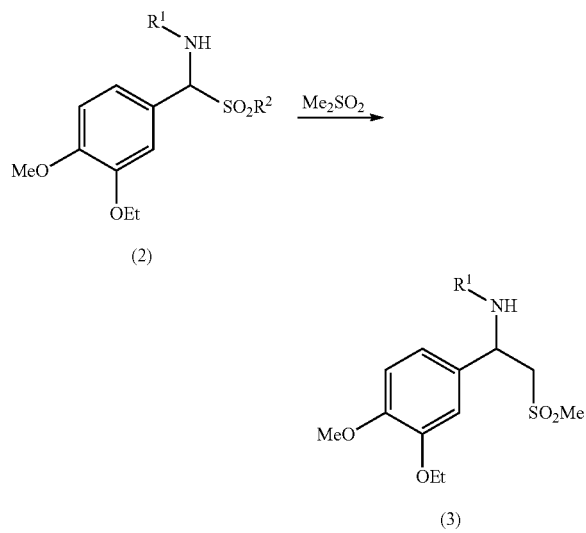

(2)

(3)

c) deprotecting sulfone (3) to obtain 1-(3-ethoxy-4-methoxyphenyl)-2-(methylsulfonyl)ethan-1-amine (1) in the form of a racemic mixture.

Amine protecting groups useful for the invention are, for example, carbamates (in which the nitrogen atom is linked to a group of formula —C(O)OR, wherein R is, e.g., methyl, ethyl, tert-butoxy, allyl, benzyl, p-methoxybenzyl, p-nitrobenzyl, p-chlorobenzyl or 2,4-dichlorobenzyl carbamate), amides (in which the nitrogen atom is linked to a group of formula —C(O)—R', wherein R' is for example hydrogen, methyl, chloromethyl, trichloromethyl, trifluoromethyl, phenyl, or benzyl) or phosphinoamides (in which the nitrogen atom is linked to a group of formula —P(O)—(R'')₂ wherein R' is, for example, aryl, preferably phenyl).

In a second aspect thereof, the invention is directed to some intermediate compounds prepared in the process described above.

DETAILED DESCRIPTION OF THE INVENTION

All terms used in the present application, unless otherwise indicated, must be interpreted in their ordinary meaning as known in the technical field. Other more specific definitions for some terms used in the present application are given below and are intended to be applied uniformly to the entire description and claims, unless otherwise indicated.

In general, the nomenclature used in this application is based on AUTONOM™ v.4.0, a Beilstein Institute computerized system for the generation of IUPAC systematic nomenclature. If there is a discrepancy between a depicted structure and a name given to that structure, the depicted structure should be considered correct. Furthermore, if the stereochemistry of a structure or a portion of a structure is not indicated with, for example, bold or dashed lines, the structure or portion of the structure has to be interpreted as encompassing all existing stereoisomers of it.

The term "racemic" refers to a sample of a chiral compound which contains both the (+) and (−) isomers in equal amounts.

The term "about" includes the range of experimental errors, which can normally occur performing a measurement.

The term "protective group" refers to moieties in a compound, which block reactive sites such as, for example, carboxyl, amino, amido or hydroxyl functions. Suitable protective groups are well known to those of ordinary skill in the art.

The term "aryl" refers to any substituent derived from a monocyclic or a polycyclic aromatic hydrocarbon by removal of a hydrogen atom from a ring carbon atom (e.g. phenyl, tolyl, 1-naphtyl or 2-napthyl).

The compounds obtained by the chemical transformations of the present invention can be used at the following steps without further purification or, optionally, can be separated and purified by employing conventional methods well known to those skilled in the art, such as solvent extraction, solvent trituration, re-crystallization, column chromatography, or by transforming them into a polymorph, a salt or in a co-crystal with an appropriate co-former, or by washing with an organic solvent or with an aqueous solution, optionally adjusting pH.

It will be understood that any compound described herein may also describe any polymorphs, salts or co-crystals thereof.

According to its most general aspect, the present invention relates to a process outlined above for preparing the beta-aminosulfone of formula (1) in racemic form.

Step a) includes the conversion of 3-ethoxy-4-methoxybenzaldehyde (9) into an aminosulfone of formula (2).

This conversion can be conveniently carried out by reacting 3-ethoxy-4-methoxybenzaldehyde (9) with a compound of formula R¹—NH₂ and a compound of formula R²—S(O)OH or a salt thereof, wherein the substituents assume the meanings reported above. Step a) is conveniently carried out in the presence of an acid, preferably selected from the group consisting of a Lewis acid (more preferably chlorotrimethylsilane) and a carboxylic acid (more preferably formic acid).

Preferably step a) is carried out in the presence of a salt of the compound of formula R²—S(O)OH (generally referred to as sulfinate). More preferably, said sulfinate is a compound of formula R²—S(O)OM, wherein the substituents assume the meanings reported above and M is an ion, such as sodium, potassium, lithium, calcium, magnesium, copper or caesium. Even more preferably said salt of the compound of formula $R^2$—S(O)OH is sodium p-toluenesulfinate. The compound of formula $R^1$—$NH_2$ is preferably selected from the group consisting of carbamates (preferably tert-butyl or benzyl carbamate); amides (e.g. formamide or acetamide); phosphinoamides (preferably diphenylphosphinoamide) and mixtures thereof.

Preferably step a) is carried out in at least one solvent, more preferably in a mixture comprising water and at least one solvent selected from the group consisting of alcohols (for example methanol, ethanol, 2-propanol, 1-butanol, 2-butanol, tert-butanol and mixtures thereof) and ethers (for example tetrahydrofuran). According to a preferred embodiment of this aspect of the invention, step a) is carried out in a mixture comprising an alcohol (preferably 1-butanol) and water, said mixture having, in an even more preferred embodiment, a ratio of the alcohol to water from about 1:0.5 vol/vol to about 1:10 vol/vol. Even more preferably, the ratio of the alcohol to water in said solvents mixture is from about 1:2 vol/vol to about 1:4 vol/vol.

In step a) the reaction temperature can be from about 0° C. to 40° C., preferably from about 10° C. to about 20° C. In general, the higher the reaction temperature, the shorter the reaction time.

The amount of acid optionally used in step a) (preferably a Lewis or a carboxylic acid) is conveniently from 1 to 2 equivalents, preferably from 1.05 to 1.50 equivalents, more preferably from 1.10 to 1.40, even more preferably from 1.15 to 1.35, with respect to the molar quantity of the starting aldehyde (9).

The compound of formula $R^2$—S(O)OH or the salt thereof are used in step a) in amounts conveniently from 1 to 2 equivalents, preferably from 1.01 to 1.50 equivalents, more preferably from 1.05 to 1.40, even more preferably from 1.08 to 1.35, with respect to the molar quantity of the starting aldehyde (9).

The amount of the compound of formula $R^1$—$NH_2$ used in step a) is conveniently from 1 to 2 equivalents, preferably from 1.01 to 1.50 equivalents, more preferably from 1.05 to 1.40, even more preferably from 1.08 to 1.35, with respect to the molar quantity of the starting aldehyde (9). The inventors have observed that, in the reaction mixture, aminosulfone (2) is in equilibrium with the starting aldehyde (9), and that the equilibrium can be shifted towards the aminosulfone (2) by allowing this compound to crystallize out from the reaction mixture, thus leading the reaction to substantial completion.

Said crystallization conditions may be easily determined by a person skilled in the art by means of a preliminary investigation including dispersing the aminosulfone (2) into the selected solvent or mixture of solvents used in step a) so as to determine its solubility equilibrium.

In one embodiment of this aspect of the invention, the precipitated aminosulfone (2) is triturated and finally washed with iso-propyl acetate.

The aminosulfone of formula (2) thus obtained, optionally isolated, is further converted into a sulfone of formula (3), according to step b).

Step b) can be performed by treating the aminosulfone of formula (2), optionally converted into the corresponding imine (10) as detailed below, with a carbanion of dimethyl sulfone to obtain compound (3). Step b) can be carried out in any suitable solvent, such as ethers (preferably diethyl ether, tetrahydrofuran, 2-methyltetrahydrofuran, methyl tert-butyl ether), N-methyl pyrrolidone, N,N-dimethylacetamide, N,N-dimethylformamide, glyme, diglyme, toluene, xylene, hexane or mixtures thereof; at a temperature from −80 to −30° C., preferably from −60 to −50° C., e.g. at −55° C.

The carbanion of dimethyl sulfone can be prepared according to standard techniques in organic synthesis, for example, by treating dimethyl sulfone with a strong base. Suitable strong bases are preferably selected from the group consisting of organolithium reagents, organomagnesium reagents or sodium, lithium, potassium or magnesium amides. The preparation of the carbanion of dimethyl sulfone normally takes place at a temperature from −80 to −30° C., for example from −60 to −50° C., in an ether (preferably tetrahydrofuran, diethyl ether, 2-methyltetrahydrofuran, methyl tert-butyl ether, bis(2-methoxyethyl) ether) optionally in mixture with a hydrocarbon (preferably hexane, toluene, or xylene). Preferably, the solvent used is a mixture of tetrahydrofuran and n-hexane.

Organolithium reagents useful for this purpose are for example n-butyllithium, sec-butyllithium, phenyllithium, neopentyllithium, propyllithium, tert-butyllithium or preferably hexyllithium; organomagnesium reagents are for example a tert-butylmagnesium or iso-propylmagnesium halide (preferably tert-butylmagnesium or iso-propylmagnesium chloride); lithium, sodium, potassium or magnesium amides are for example selected from the group consisting of sodium, lithium or potassium bis(trimethylsilyl)amide (NaHMDS, LiHMDS or KHMDS), lithium diisopropylamide (LDA) or magnesium bis(diisopropylamide) (MDA).

In the case when an organomagnesium reagent is used to prepare the carbanion of dimethyl sulfone, convenient reaction conditions include the presence of at least one alkali halide (preferably a chloride), for example a lithium, sodium, potassium or caesium chloride, or of a halide of zinc or copper. More preferably the carbanion of dimethyl sulfone is prepared by means of a mixture of iso-propylmagnesium chloride and lithium chloride.

Alternatively said carbanion can be prepared by treating dimethyl sulfone with a hydride (preferably sodium, lithium or potassium hydride) or an alkali metal tert-butoxide (such as sodium or potassium tert-butoxide) at a temperature from −40 to 50° C., for example from −30 to 40° C., in an ether (preferably tetrahydrofuran), in N,N-dimethylacetamide or in N,N-dimethylformamide.

The strong base is preferably used in stoichiometric amount with respect to the molar amount of dimethyl sulfone used.

The molar ratio of the carbanion of dimethyl sulfone with respect to the aminosulfone of formula (2) is normally from 1 to 6, preferably from 3 to 4.

In a possible variant of this operation, the aminosulfone of formula (2) is converted into the corresponding imine (10):

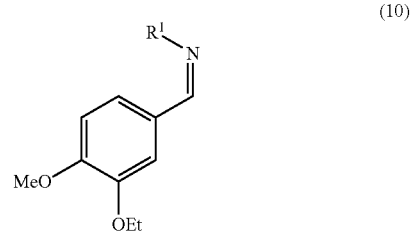

(10)

wherein $R^1$ can assume any of the meanings given above; which is subsequently treated with the carbanion of dimethyl sulfone to obtain compound (3). Said imine (10) can be, for example, prepared by treating the aminosulfone (2) with one of the bases listed above to operate step b). Alternatively said step can be performed by treating the aminosulfone (2) with a hydroxide or a carbonate of an alkali metal (such as $K_2CO_3$, $Na_2CO_3$, $Li_2CO_3$, $Cs_2CO_3$, KOH, NaOH, LiOH) in a water miscible solvent (e.g. methanol, ethanol, tetrahydrofuran, dimethoxyethane, dioxane or a mixture thereof) optionally in mixture with water. The amount of the hydroxide or carbonate of the alkali metal used is normally from 1 to 5 equivalents, preferably from 1.5 to 2 equivalents, compared to the molar quantity of the aminosulfone (2) used.

Preferably the carbanion of dimethyl sulfone used in step b) is $LiCH_2SO_2Me$, more preferably $LiCH_2SO_2Me$ prepared in situ by reacting $Me_2SO_2$ with nBuLi or, even more preferably, with nHexLi.

Preferably, in the case when nHexLi is used to prepare the carbanion of dimethyl sulfone, the ratio of intermediate (2) to dimethyl sulfone and nHexLi is from 1:2:2 to 1:6:6 on molar basis, preferably about 1:4:4 on molar basis.

The following step c), entails the conversion of sulfone (3), optionally isolated, into a racemic mixture of 1-(3-ethoxy-4-methoxyphenyl)-2-(methylsulfonyl)ethan-1-amine (1). This operation can be performed using any one of the methods generally known in the field to remove an amino protecting group, for example one of those described in Theodora W. Green, *Protective Groups in Organic Synthesis*, John Wiley & Sons (1999), pages 503-598, which are herein incorporated by reference. Preferably, in the case where R1 forms, together with the nitrogen atom to which it is linked, a carbamate group, said de-protection step may be operated according to the procedures detailed on pages 504-540 of the text referred to above, while, in the case where $R^1$ forms, together with the nitrogen atom to which it is linked, an amide or a phosphinoamide group, said de-protection step can be carried out according to the procedures reported respectively on pages 551-561 and 598 of the same text. According to an even more preferred embodiment of this aspect of the invention, in the case where $R^1$ is a benzyloxycarbonyl group, step c) can be carried out by treatment with hydrogen in the presence of a catalyst (e.g. palladium, platinum or nickel) optionally supported on an appropriate carrier, such as carbon or barium carbonate, in an alcohol (preferably methanol or ethanol) or a mixture thereof with water. Conversely, when $R^1$ is a tert-butoxycarbonyl group, it can be carried out according to one of the procedures described in Theodora W. Green, *Protective Groups in Organic Synthesis*, John Wiley & Sons (1999), pages 520-522. Preferably, step c) is performed by treating sulfone (3) with a solution of hydrogen chloride in water or in an organic solvent.

Compound (1) can be separated and purified by employing conventional methods well known to those skilled in the art, such as solvent extraction with an organic solvent or with an aqueous solution optionally adjusting pH, solvent trituration, crystallization or combination thereof. In one embodiment, compound (1) is extracted and then crystallized from 1-butanol.

Compound (1) obtained according to the embodiments of the present invention is in the form of a racemic mixture, which can, in a further optional step, be separated into the corresponding an enantiomerically enriched or an enantiomerically pure form thereof.

In a second aspect thereof, the invention encompasses some intermediate compounds prepared in the process described above.

Particularly, the invention is directed to the imine of formula (10), the aminosulfone of formula (2), and the sulfone of formula (3).

The use of any one of the compounds of formulae (2), (3), and (10) for preparing Apremilast, an optical isomer, a solvate, a hydrate, or any intermediates in the synthesis thereof is a further aspect of the present invention.

The invention will be further illustrated by the following examples.

Example 1

This example is representative of step a) of the present invention.

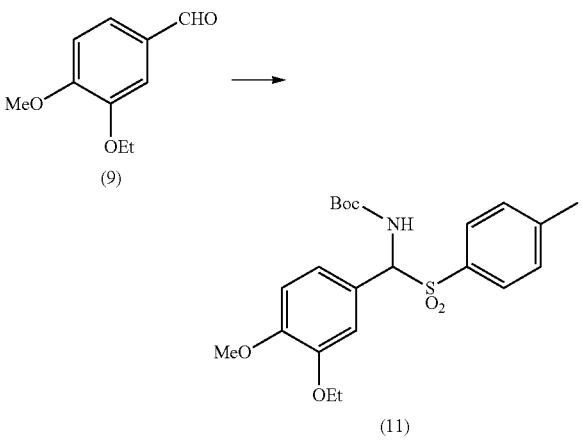

In a 3 L glass jacketed reactor, equipped with mechanical stirrer, thermometer, condenser and kept under inert gas, were charged at 20-25° C. 3-ethoxy-4-methoxybenzaldehyde (200 g), tert-butyl carbamate (144 g), sodium p-toluenesulfinate (216 g), 1-butanol (130 mL) and water (1080 mL). Addition of the solvents onto the solids resulted in a latent endotherm of the system (endothermic dissolution). Under stirring, the temperature was adjusted at 20-25° C., 68 g of formic acid were added and the system was maintained under these conditions for additional 48 hours, in order for the intermediate product (11) to precipitate abundantly. The system was then diluted with 800 mL of water and maintained under stirring for additional 24 hours.

After cooling down to 0-5° C., a 15% (w/w) sodium hydrogen carbonate aqueous solution up to a stable pH of 7.0-7.3 was slowly added to the suspension. The resulting mixture was finally filtered under reduced pressure and the wet cake washed with 3×100 mL of water. The wet solid was charged in the same reactor again, and 1200 mL of isopropyl acetate were added. The resulting suspension was stirred for one hour at 20-25° C., then filtered and the wet cake washed with 3×60 mL of isopropyl acetate. The final product was dried under vacuum at 40° C., thus affording 300 g of intermediate (11).

Example 2

This example is representative of steps b) and c) of the present invention.

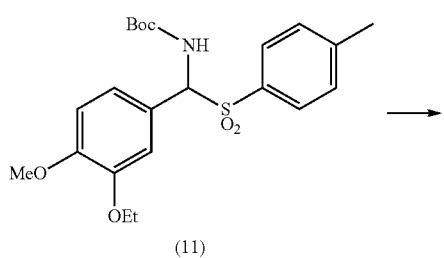

(11)

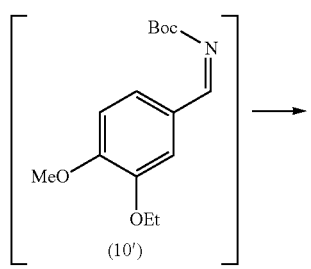

(10')

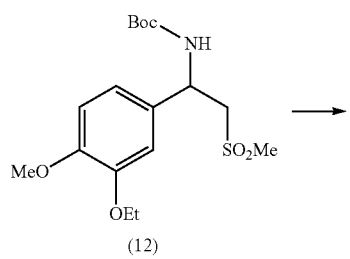

(12)

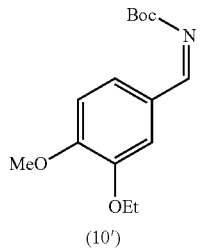

(1)

Dimethyl sulfone (310 g) and tetrahydrofuran (1800 mL) were charged at 20-25° C. to a 10 L glass jacketed reactor equipped with mechanical stirrer, thermometer, condenser and kept under inert gas. Resulting suspension was cooled down to −60° C. Under stirring, n-hexyl lithium (2.3 M solution in hexane, 1440 mL) was added at a rate such that the reaction temperature did not exceed −40° C. (exothermic reaction). A previously prepared solution of activated intermediate (11) (360 g) in tetrahydrofuran (3600 mL) was then added to the reactor at such a rate that the reaction temperature did not exceed −55° C. At the end of the addition, the system was maintained at −55° C. for one additional hour. Then the mass was quickly poured into another reactor containing 1260 mL of water at 20-25° C. The reactor was rinsed with 360 mL of tetrahydrofuran and the rinsing was combined to the quenched mixture. Temperature of the mass was adjusted to 20-25° C. and the layers were allowed to separate. Bottom aqueous phase was transferred into another suitable reactor and counter-extracted with 540 mL of toluene at 45-50° C. Combined organic layers were concentrated under reduced pressure (25-40 mbar; T=50-55° C.) down to a viscous residue.

After having added toluene (1080 mL), water (270 mL) and hydrochloric acid (12N, 170 g), the resulting solution was heated up to 65-70° C. and maintained under stirring at these conditions for additional one hour. The mixture was cooled down to 25-30° C. and the layers were allowed to separate. Bottom aqueous layer was transferred into another reactor, where 1440 mL of 1-butanol and 240 g of 30% (w/w) sodium hydroxide aqueous solution were added, keeping the internal temperature below 50° C. Temperature of the mass was adjusted to 45-50° C. and the layers were allowed to separate. Bottom aqueous phase was transferred into another suitable reactor and counter-extracted with 180 mL of 1-butanol. Combined organic layers were concentrated under reduced pressure (25-40 mbar; T=55-60° C.) to a viscous residue. The mass was diluted with 540 mL of 1-butanol, heated up to 75-80° C. and filtered through a celite pad in order to remove insoluble particles. Reactor and lines were rinsed with 180 mL of 1-butanol and the combined alcoholic phases were allowed to cool down to 0-5° C. in order for compound (1) to crystallize. The obtained solid was filtered, the wet cake washed with 2×180 mL of 1-butanol and the final product dried under vacuum at 45-50° C., thus affording 145 g of compound (1).

$^1$H NMR (CDCl$_3$): δ1.43-1.46 (t, 3H), 2.88 (s, 3H), 3.18-3.32 (m, 2H), 3.83 (s, 3H), 4.07-4.11 (q, 2H), 4.55-4.58 (d, 1H), 6.81-6.89 (m, 3H), 8.71 (2H).

Example 3

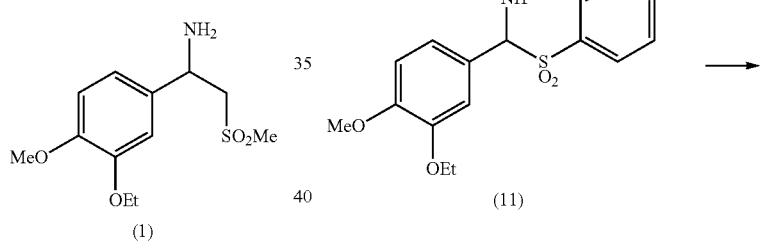

(11)

Intermediate (11) (10 g) 1 and tetrahydrofuran (100 mL) were charged at 20-25° C. in a 250 mL glass flask equipped with mechanical stirrer, thermometer, and condenser. Potassium carbonate (19 g) and sodium sulfate (1.7 g) were added thereto, then the resulting suspension was maintained under stirring at 60-65° C. until complete was achieved (about 3 hours). The mixture was cooled to 20-25° C. and filtered. The filtrate was concentrated under reduced pressure to a residue which was crystallized from iso-propylacetate thus yielding 5.77 g of compound (10').

The invention claimed is:

1. A process for preparing racemic beta-aminosulfone of formula (I),

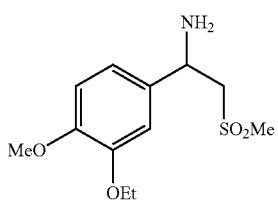

the process comprising:
a) reacting 3-ethoxy-4-methoxybenzaldehyde of formula (9) with a compound of formula $R^1$—$NH_2$ and a compound of formula $R^2$—S(O)OH or a salt thereof to obtain an aminosulfone of formula (2):

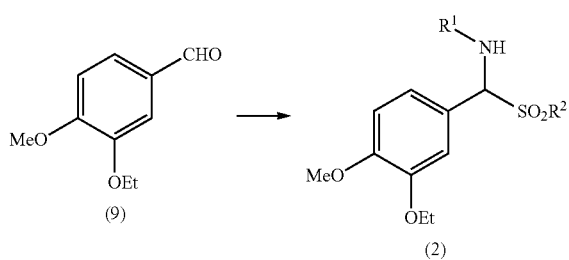

wherein:
$R^1$ is an amino protecting group; and
$R^2$ is a C1-C6 alkyl, a substituted C1-C6 alkyl, a C6-C10 aryl or a substituted C6-C10 aryl;
b) converting the aminosulfone of formula (2) into a sulfone of formula (3) by treatment with a carbanion derived from dimethyl sulfone:

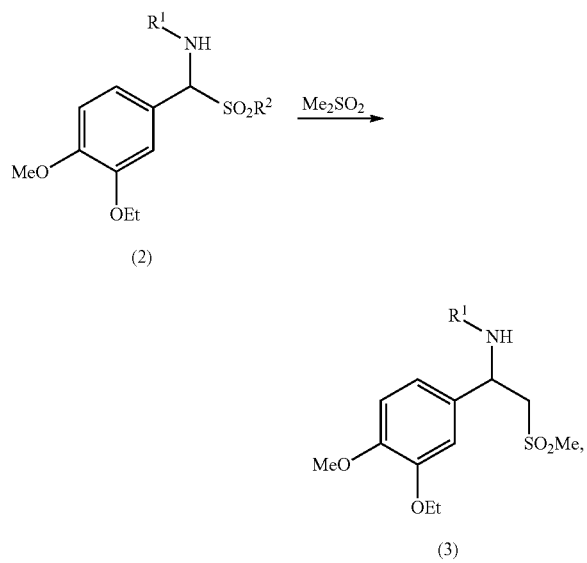

and
c) deprotecting the sulfone of formula (3) to obtain 1-(3-ethoxy-4-methoxyphenyl)-2-(methylsulfonyl) ethan-1-amine of formula (1) in the form of a racemic mixture.

2. The process according to claim 1, wherein, in step a), the compound of formula $R^2$—S(O)OH is a sulfinate.

3. The process according to claim 1, wherein, in step a), the compound of formula $R^2$—S(O)OH is sodium p-toluenesulfinate.

4. The process according to claim 1, wherein step a) is performed in the presence of an acid.

5. The process according to claim 4, wherein the acid is selected from the group consisting of carboxylic acids and Lewis acids.

6. The process according to claim 4, wherein acid is formic acid.

7. The process according to claim 1, wherein, in step a), the amino protecting group is a tert-butoxycarbonyl group or a benzyloxycarbonyl group.

8. The process according to claim 1, wherein, in step a), the amino protecting group is a formyl group or an acetyl group.

9. The process according to claim 1, wherein, in step b), the process further comprises preparing the carbanion derived from dimethyl sulfone by treating dimethyl sulfone with a base selected from the group consisting of organolithium reagents, organomagnesium reagents, sodium amides, lithium amides, potassium amides, and magnesium amides.

10. The process according to claim 9, wherein, in step b), the base is selected from the group consisting of n-butyllithium, sec-butyllithium, phenyllithium, neopentyllithium, propyllithium, tert-butyllithium, and hexyllithium.

11. The process according to claim 1, wherein step b) comprises converting the aminosulfone of formula (2) produced in step a) into the corresponding imine of formula (10) by treatment with a base:

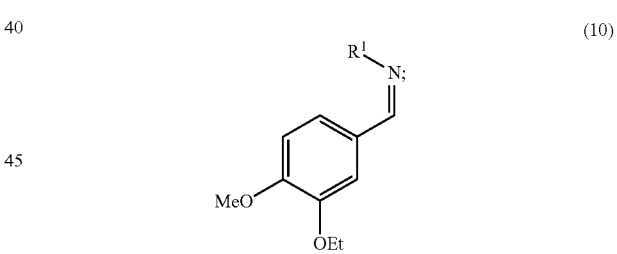

and subsequently, treating the imine of formula (10) with carbanion derived from dimethyl sulfone to obtain a compound of formula (3).

12. The process according to claim 11, wherein the base is selected from the group consisting of hydroxides and carbonates of alkali metals.

13. The process according to claim 11, wherein the same base is used for converting the aminosulfone of formula (2) into the imine (10) and for preparing the carbanion derived from dimethyl sulfone.

14. The process according to claim 1, wherein, when $R^1$ is a tert-butoxy carbonyl group, the deprotecting of step c) is accomplished with hydrochloric acid.

15. The process according to claim 1, wherein the process further comprises converting racemic 1-(3-ethoxy-4-methoxyphenyl)-2-(methylsulfonyl)ethan-1-amine of formula (1) into an enantiomerically enriched or an enantiomerically pure form thereof.

16. An Imine of formula (10):

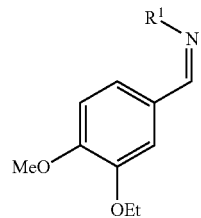

(10)

wherein R¹ is an amino protecting group which forms, together with the nitrogen atom to which it is linked, a carbamate, an amide, or a phosphinoamide group.

17. Sulfone of formula (3):

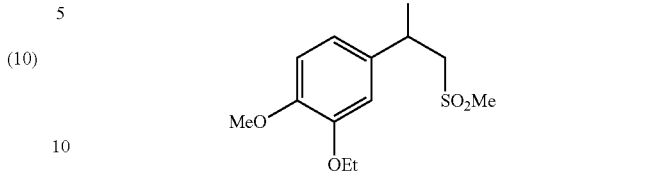

(3)

wherein R¹ is a tert-butoxycarbonyl or a benzyloxycarbonyl group.

18. The process according to claim 15, wherein the process further comprises converting the enantiomerically enriched or the enantiomerically pure form of 1-(3-ethoxy-4-methoxyphenyl)-2-(methylsulfonyl)ethan-1-amine (1) into Apremilast, an optical isomer thereof, a solvate thereof, or a hydrate thereof.

* * * * *